United States Patent [19]

Kuwatsuka et al.

[11] Patent Number: 5,136,042
[45] Date of Patent: Aug. 4, 1992

[54] PROCESS FOR THE PREPARATION OF THIAZOLECARBOXYLIC ACID CHLORIDES

[75] Inventors: Toshiaki Kuwatsuka; Seiichi Watanabe, both of Mobara; Yoshinori Tanaka, Yokohama; Toshiyuki Kouno, Chosei; Katsutoshi Ishikawa, Ashigarashimo, all of Japan

[73] Assignee: Mitsui Toatsu Chemicals, Inc., Tokyo, Japan

[21] Appl. No.: 465,167

[22] PCT Filed: Jun. 1, 1989

[86] PCT No.: PCT/JP89/00549
§ 371 Date: Feb. 1, 1990
§ 102(e) Date: Feb. 1, 1990

[87] PCT Pub. No.: WO89/12047
PCT Pub. Date: Dec. 14, 1989

[30] Foreign Application Priority Data

Jun. 3, 1988 [JP] Japan ................... 63-136689
Jun. 20, 1988 [JP] Japan ................... 63-150183

[51] Int. Cl.⁵ .................... C07D 277/04; C07D 277/18
[52] U.S. Cl. .................... 548/188; 548/200
[58] Field of Search .................... 548/188, 200

[56] References Cited

U.S. PATENT DOCUMENTS 3,154,578 10/1964 Kinnel et al. .................... 548/200

Primary Examiner—Mary C. Lee
Assistant Examiner—Robert C. Whittenbough
Attorney, Agent, or Firm—Cushman, Darby & Cushman

[57] ABSTRACT

Disclosed herein is a process for the preparation of a thiazolecarboxylic acid chloride represented by the following general formula (II):

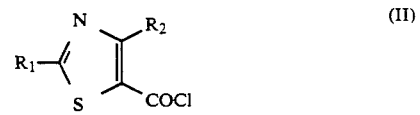

wherein $R_1$ represents a hydrogen or halogen atom, a lower alkyl group, a lower alkoxy group, or a lower alkyl group substituted by a halogen atom or lower alkoxy group, and $R_2$ represents a hydrogen atom, a lower alkyl group, or a lower alkyl group substituted by a halogen atom or lower alkoxy group, which comprises reacting a thiazolecarboxylic acid represented by the following general formula (I):

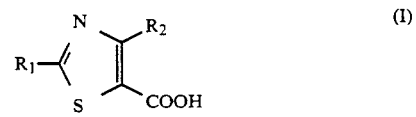

wherein $R_1$ and $R_2$ have the same meanings as defined with respect to formula (II), with phosgene or trichloromethyl chloroformate in the presence or absence of a catalyst.

8 Claims, No Drawings

PROCESS FOR THE PREPARATION OF THIAZOLECARBOXYLIC ACID CHLORIDES

TECHNICAL FIELD

The present invention relates to a process for the preparation of thiazolecarboxylic acid chlorides which are useful as starting materials for pharmaceutical products, agricultural chemicals, etc.

BACKGROUND ART

Known conventional processes for the preparation of thiazolecarboxylic acid chlorides include the process using thionyl chloride (Journal of Chemical Society, 1945, 601), (Journal of Heterocyclic Chemistry, 22, 1621 (1985)) and the process employing oxalyl chloride (Journal of Chemical Society Perkin 1, 159, (1982).

In the process making use of thionyl chloride, one or more side reactions occur when the starting thiazolecarboxylic acid is a 2-alkylthiazolecarboxylic acid. It is therefore necessary to maintain the reaction temperature at an extremely low level. A further limitation is imposed on the solvent. The yield is however extremely low even under such reaction conditions.

When a starting material other than 2-alkyl-thiazolecarboxylic acids is employed on the other hand, thionyl chloride undergoes an extremely vigorous reaction with the thiazolecarboxylic acid as the starting material so that the reaction can hardly be controlled. Further, the reaction is accompanied by rapid evolution of heat and immense production of corrosive sulfurous acid gas. As an industrial preparation process, this process therefore involves problems such that extra apparatus and labor are required for the processing of the sulfurous acid gas produced in a large volume.

The process in which oxalyl chloride is used is uneconomical for industrial applications because oxalyl chloride is costly. In addition, this process requires a long reaction time unless a catalyst is employed.

DISCLOSURE OF THE INVENTION

An object of this invention is to obtain a thiazolecarboxylic acid chloride at high purity and yield without need for processing of byproducts while enjoying easy controllability of the reaction.

In order to attain the above object, the present inventors have carried out an extensive investigation with respect to the problems described above. This has resulted in the finding of a preparation process in which a thiazole carboxylic acid is reacted with phosgene or trichloromethyl chloroformate, leading to the completion of the present invention.

Namely, this invention provides a process for the preparation of a thiazolecarboxylic acid chloride represented by the following general formula (II):

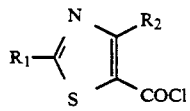

wherein $R_1$ represents a hydrogen or halogen atom, a lower alkyl group, a lower alkoxy group, or a lower alkyl group substituted by a halogen atom or lower alkoxy group, and $R_2$ represents a hydrogen atom, a lower alkyl group, or a lower alkyl group substituted by a halogen atom or lower alkoxy group—hereinafter called the "thiazole-carboxylic acid chloride" —, which comprises reacting a thiazolecarboxylic acid represented by the following general formula (I):

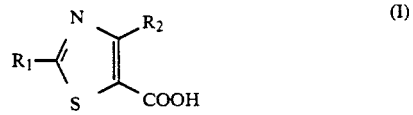

wherein $R_1$ and $R_2$ have the same meanings as defined with respect to formula (II) —hereinafter called the "thiazolecarboxylic acid" -, with phosgene or trichloromethyl chloroformate in the presence or absence of a catalyst.

According to the process of the present invention, the desired thiazolecarboxylic acid can be obtained at higher purity and yield compared to the conventional techniques.

BEST MODE FOR CARRYING OUT THE INVENTION

As thiazolecarboxylic acids useful as starting materials in the process of the present invention, may be mentioned for example thiazole-5-carboxylic acid, 2-methylthiazole-5-carboxylic acid, 2-ethylthiazole-5-carboxylic acid, 2-iso-propylthiazole-5-carboxylic acid, 2-n-propylthiazole-5-carboxylic acid, 2-n-butylthiazole-5-carboxylic acid, 2-iso-butylthiazole-5car acid, 2-sec-butylthiazole-5-carboxylic acid, 2-tert-butyl-thiazole-5-carboxylic acid, 2-n-pentyl-thiazole-5-carboxylic acid, 2-n-hexylthiazole-5carboxyl acid, 2-fluorothiazole-5-carboxylic acid, 2-chlorothiazole-5-carboxylic acid, 2-bromothiazole-5carboxylic acid, 2-iodothiazole-5-carboxylic acid, 2-methoxythiazole-5-carboxylic acid, 2-ethoxythiazole- 5-carboxylic acid, 2-(n-propoxy)thiazole-5-carboxylic acid, 2-(iso-propoxy)thiazole-5-carboxylic acid, -chloromethylthiazole-5-carboxylic acid, 2-trichloro-methylthiazole- 5-carboxylic acid, 2-fluoromethyl-thiazole-5-carboxylic acid, 2-trifluoromethylthiazole-carboxylic acid, 2-bromomethylthiazole-5-carboxylic acid, 2-iodomethylthiazole-5-carboxylic acid, 2-($\beta,\beta,\beta$-trifluoroethyl)thiazole-5-carboxylic acid, -methoxymethylthiazole-5-carboxylic acid, 2-ethoxy-methylthiazole-5-carboxylic acid, 4-methylthiazole-5-carboxylic acid, 4-ethylthiazole-5-carboxylic acid, -iso-propylthiazole-5-carboxylic acid, 4-n-propyl-thiazole-5-carboxylic acid, 4-n-butylthiazole-5-carboxylic acid, 4-iso-butylthiazole-5-carboxylic acid, -sec-butylthiazole-5-carboxylic acid, 4-tert-butyl-thiazole-5-carboxylic acid, 4-n-pentylthiazole-5carboxylic acid, 4-n-hexylthiazole-5-carboxylic acid, -chloromethylthiazole-5-carboxylic acid, 4-trichloro-thiazole-5-carboxylic acid, 4-fluoromethylthiazole-5-carboxy acid, 4-trifluoromethylthiazole-5-carboxylic acid, 4-bromomethylthiazole-5-carboxylic acid, 4-iodomethyltriazole-5-carboxylic acid, 4-($\beta,\beta,\beta$-trifluoroethyl)thiazole-5-carboxylic acid, 4-methoxymethylthiazole-5-carboxylic acid, 4-ethoxymethylthiazole-5carboxylic acid, 2,4-dimethylthiazole-5-carboxylic acid, 2,4-diethylthiazole-5-carboxylic acid, 2,4-di-(n-propyl)thiazole-5-carboxylic acid, 2,4-di-(iso-propyl)-thiazole-5-carboxylic acid, 2,4-di-(n-butyl)- thiazole-5-carboxylic acid, 2,4-di-(iso-butyl)thiazole-5-carboxylic acid, 2,4-di-(sec-butyl)thiazole-5-carboxylic acid, 2,4-di-(tert-butyl)thiazole-5-carboxylic acid, 2,4-di-(n-pentyl)-thiazole-5-carboxylic acid, 2,4-di-(n-hexyl)thiazole-5-carboxylic acid, 2,4- di-(chloromethyl)thiazole-5-carboxylic acid, 2,4-di-(fluoromethyl)thiazole-5-carboxylic acid, 2,4-di-(tri-fluoromethyl)thiazole-5-carboxylic acid, 2,4-di-(tri-chloromethyl)thiazole-5-carboxylic acid, 2,4-di-(bromo-methyl)thiazole-5-carboxylic acid, 2,4-di-(iodomethyl)-thiazole-5-carboxylic acid, 2,4-di-(8,6,8-trifluoro-ethyl)thiazole-5-carboxylic acid, 2,4-di-(methoxy-methyl)thiazole-5-carboxylic acid, 2,4-di-(ethoxy-methyl)thiazole-5-carboxylic acid, 2-methyl-4-ethyl-thiazole-5-carboxylic acid, 2-methyl-4-iso-propyl-thiazole-5-carboxylic acid, 2-methyl-4-n-propyl-thiazole-5-carboxylic acid, 2-methyl-4-n-butylthiazole-5-carboxylic acid, 2-methyl-4-iso-butylthiazole-5carboxyl acid, 2-methyl-4-sec-butylthiazole-5carboxylic acid, 2-methyl-4-tert-butylthiazole-5-carboxylic acid, 2-methyl-4-n-pentylthiazole-5carboxylic acid, 2-methyl-4-n-hexylthiazole-5carboxylic acid, 2-methyl-4-chloromethylthiazole-5carboxylic acid, 2-methyl-4-fluoromethylthiazole-5carboxylic acid, 2-methyl-4-trifluoromethylthiazole-5carboxylic acid, 2-methyl-4-trichloromethylthiazole-5carboxylic acid, 2-methyl-4-bromomethylthiazole-5carboxylic acid, 2-methyl-4-iodomethylthiazole-5-carboxylic acid, 2-methyl-4-(β,β,β-trifluoroethyl)-thiazole-5-carboxylic acid, 2-methyl-4-methoxymethyl-thiazole-5-carboxylic acid, 2-methyl-4-ethoxymethyl-thiazole-5-carboxylic acid, 2-ethyl-4-methylthiazole5-carboxylic acid, 2-ethyl-4-n-propylthiazole-5carboxylic acid, 2-ethyl-4-isopropylthiazole-5carboxylic acid, 2-ethyl-4-n-butylthiazole-5-carboxylic acid, 2-ethyl-4-fluoromethylthiazole-5-carboxylic acid, 2-ethyl-4-trifluoromethylthiazole-5-carboxylic acid, 2-ethyl-4-chloromethylthiazole-5-carboxylic acid, 2-ethyl-4-methoxymethylthiazole-5-carboxylic acid, 2propyl-4-methylthiazole-5-carboxylic acid, 2-iso-propyl-4-ethylthiazole-5-carboxylic acid, 2-iso-propyl-4-n-propylthiazole-5-carboxylic acid, 2-iso-propyl-4-n-butylthiazole-5-carboxylic acid, 2-iso-propyl-4-fluoromethylthiazole-5-carboxylic acid, 2-iso-propyl-4-trifluoromethylthiazole-5-carboxylic acid, 2-iso-propyl-4-chloromethylthiazole-5-carboxylic acid, 2-iso-propyl-4-methoxymethylthiazole-5-carboxylic acid, propyl-4-ethylthiazole-5-carboxylic acid, 2-n-propyl-4-iso-propylthiazole-5-carboxylic acid, 2-n-propyl-5-carboxylic acid, 2-n-propyl-4-fluoro-methylthiazole-5-carboxylic acid, 2-n-propyl-4-trifluoromethyl-thiazole-5-carboxylic acid, 2-n-propyl-4-methoxyme-thylthiazole- 5-carboxylic acid, 2-tert-butyl-4-methyl-thiazole-5-carboxylic acid, 2-tert-butyl4-ethylthiazole-5-carboxylic acid, 2-tert-butyl-4-propylthiazole-5-carboxylic acid, 2-tert-butyl-4-trifluromethylthiazole-5-carboxylic acid, 2-tert-butyl4-methoxymethylthiazole-5-carboxylic acid, 2-fluoro-4-methylthiazole-5-carboxylic acid, 2-fluoro-4-ethyl thiazole-5-carboxylic acid, 2-fluoro-4-n-propyl-thiazole-5-carboxylic acid, 2-fluoro-4-iso-propyl-thiazole-5-carboxylic acid, 2-fluoro-4-n-butylthiazole5-carboxylic acid, 2-fluoro-4-tert-butylthiazole-5carboxylic acid, 2-fluoro-4-trifluoromethylthiazole-5carboxylic acid, 2-fluoro-4-(β,β,β-trifluoroethyl)-thiazole-5-carboxylic acid, 2-chloro-4-methylthiazole5-carboxylic acid, 2-chloro-4-ethylthiazole-5carboxylic acid, 2-chloro-4-iso-propylthiazole-5carboxylic acid, 2-chloro-4-n-propylthiazole-5carboxylic acid, 2-chloro-4-n-butylthiazole-5carboxylic acid, 2-chloro-4-n-hexylthiazole-5carboxylic acid, 2-chloro-4-methoxymethylthiazole-5-carboxylic acid, 2-chloro-4-chloromethylthiazole-5carboxylic acid, 2-chloro-4-trifluoromethylthiazole-5carboxylic acid, 2-bromo-4-methylthiazole-5-carboxylic acid, 2-bromo-4-n-propylthiazole-5-carboxylic acid, 2-bromo-4-n-pentylthiazole-5-carboxylic acid, 2-iodo4-methylthiazole-5-carboxylic acid, 2-iodo-4-ethyl-thiazole-5-carboxylic acid, 2-methoxy-4-methylthiazole5-carboxylic acid, 2-methoxy-4-ethylthiazole-5carboxylic acid, 2-methoxy-4-iso-propylthiazole-5carboxylic acid, 2-methoxy-4-n-propylthiazole-5carboxylic acid, 2-mathoxy-4-sec-butylthiazole-5carboxylic acid, 2-methoxy-4-trifluoromethylthiazole-5carboxylic acid, 2-methoxy-4-methoxymethylthiazole-5carboxylic acid, 2-chloromethyl-4-methylthiazole-5carboxylic acid, 2-chloromethyl-4-ethylthiazole 5carboxylic acid, 2-chloromethyl-4-ethylthiazole-5carboxylic acid, 2-chloromethyl-4-n-butylthiazole-5carboxylic acid, 2-chloromethyl-4-chloromethylthiazole5-carboxylic acid, 2-chloromethyl-4-trichloromethyl-thiazole-5-carboxylic acid, 2-chloromethyl-4-(β,β,β-trifluoromethyl) thiazole-5-carboxylic acid, 2-tri-fluoromethyl-4-methyl-thiazole-5-carboxylic acid, 2-trifluoromethyl-4-ethyl-thiazole-5-carboxylic acid, 2-trifluoromethyl-4-fluoromethylthiazole-5-carboxylic acid, 2-tri-fluoromethyl-4-(β,β,β-trifluoromethyl)-thiazole-5-carboxylic acid, 2-trifluoromethyl-4-methoxymethyl-thiazole-5-carboxylic acid, 2-methoxy-methyl-4-methylthiazole-5-carboxylic acid, 2-methoxy-methyl-4-ethylthiazole-5-carboxylic acid, 2-methoxy-methyl-4-iso-propylthiazole-5-carboxylic acid, 2-methoxymethyl-4-tert-butylthiazole-5-carboxylic acid , 2-methoxymeth-yl-4-trifluoromethylthiazole-5-carboxylic acid, 2-methoxymethyl-4-methoxymethylthiazole-5-carboxylic acid, etc. It should however be borne in mind that the thiazolecarboxylic acid is not necessarily limited to the compounds exemplified above.

It is preferable to conduct the reaction of this invention in a solvent so that the reaction may proceed in the state of a solution or suspension.

Any solvent can be used so long as it is inert to the reaction. Illustrative of the solvent include aromatic hydrocarbons such as benzene, toluene and xylene; ethers such as tetrahydrofuran, ethylene glycol dimethyl ether and dioxane; esters such as ethyl acetate, butyl acetate and ethyl propionate; and halogenated hydrocarbons such as tetrachloroethylene and chlorobenzene. It should however be borne in mind that the solvent is not necessarily limited to the compounds exemplified above. Further, two or more of these solvents may be mixed together for use as a reaction solvent.

Regarding the amount of the solvent to be added, it is efficient to use the solvent in a volume of 0.5–10 l, preferably 0.8–5 l per mole of the thiazole-carboxylic acid.

As to the amount of phosgene or trichloromethyl chloroformate to be added relative to the thiazole-carboxylic acid, the former can be added in an amount of 0.5–10.0 moles, preferably 1.0–5.0 moles per mole of the thiazole carboxylic acid.

As to the reaction temperature, the reaction can be conducted between 20° C. and the boiling point of the solution or suspension.

The reaction time can be 5–50 hours, preferably 8–20 hours, both under heating and reflux when phosgene is blown into the solution or suspension of the thiazolecarboxylic acid. On the other hand, when trichloromethyl formate is added dropwise to the solution or suspension of the thiazolecarboxylic acid, the reaction time can be 2–40 hours, preferably 5–20 hours, both under heating and reflux.

Further, the reaction time can be shortened by using a catalyst in the present reaction.

Catalysts useful in the invention include formamides such as N,N-dimethylformamide, N-methylformanilide, N-formylpiperidine, N-formylmorpholine, N,N-dibenzylformamide, N-methyl-N-ethylformamide, N-propyl-N-n-butylformamide, N,N-di-o-toluylformamide, N,N-di-p-toluylformamide, N,N-dipentylformamide, N-formyl-piperazine, N-formylpyrrolidine and N-formylimida-zolidine; amides such as N,N-dimethylacetamide, N,N-di-n-propylacetamide, N,N-di-isopropylacetamide, N,Ndiethylpropionamide, N,N-dimethylbutylamide and N-methylacetanilide; organic bases such as pyridine, picoline, N,N-dimethylaniline, N,N-diethylaniline, triethylenediamine and triethylamine; and phosphoramide such as hexamethylphosphoramide.

The catalyst can be used in a proportion of 0.05-10 wt. % based on the thiazolecarboxylic acid, with 0.1-1 wt. % being preferred. The reaction proceeds slower when the catalyst is used too little, while the purity of the thiazolecarboxylic acid chloride is reduced due to formation of byproducts when the catalyst is used too much.

Addition of the catalyst results in a shortened reaction time, and when phosgene is blown into a solution of the thiazolecarboxylic acid, 1-20 hours are sufficient as the reaction time under heating and reflux, with 2-8 hours being preferred. When trichloromethyl chloroformate is added dropwise to a solution of the thiazolecarboxylic acid, 1-20 hours are also sufficient as the reaction time under heating and reflux, with 2-8 hours being preferred.

After completion of the reaction, an insoluble matter consisting primarily of unreacted thiazolecarboxylic acid is filtered off and the filtrate is then concentrated, whereby the thiazolecarboxylic acid chloride can be obtained easily.

The resultant thiazolecarboxylic acid chloride can be used in a next step as an intermediate for a pharmaceutical product or agricultural chemical without need for purification.

The purity of the thiazolecarboxylic acid chloride is analyzed by gas chromatography.

In a preferred embodiment, the present invention can be practiced in the following manner.

A reactor equipped with a thermometer, a stirrer and a condenser is charged with a predetermined amount of the thiazolecarboxylic acid and if necessary a specific catalyst and a particular solvent. Into the resultant solution or suspension, phosgene is blown or trichloromethyl chloroformate is added dropwise to react them under reflux at a desired temperature for a predetermined time.

After completion of the reaction, the reaction mixture is filtered and the filtrate is then concentrated, thereby making it possible to obtain the intended thiazolecarboxylic acid chloride.

Incidentally, the distillate which is obtained during the concentration can be recycled back as a solvent to the reaction system.

The present invention will hereinafter be described more specifically by the following Examples.

EXAMPLE 1

In a 300-ml three-neck flask, 7.9 g (0.5) mole) of 2,4-dimethylthiazole-5carboxylic acid were suspended in 200 ml of xylene and under heating and reflux, phosgene was blown at a flow rate of 340 ml/hr for 12 hours (0.18 mole). After completion of the reaction, the reaction mixture was filtered and the filtrate was concentrated to obtain 8.2 g of 2,4-dimethylthiazole-5-carboxylic acid chloride. Its purity and yield were 95.0% and 98.0%, respectively.

EXAMPLE 2

In a similar apparatus to Example 1, 10.7 g (0.06 mole) of 2-chloror-4methylthiazole-5carboxylic acid were suspended in 200 ml of butyl acetate. Under heating and reflux, 23.7 g (0.12 mole) of trichloro-methyl chloroformate were added dropwise over 20 hours. After completion of the dropwise addition, stirring was continued for additional 2 hours. After completion of the reaction, the reaction mixture was filtered and the filtrate was concentrated to obtain 12.1 g of 2-chloro-4-methylthiazole-5carboxylic acid chlroide. Its purity and yield were 94.0% and 95.0%, respectively.

EXAMPLE 3

In a similar apparatus to Example 1, 4.2 g (0.02 mole) of 2-trifluoromethyl-4-methylthiazole-5-carboxylic acid were suspended in 100 ml of dioxane. Under heating and reflux, 4.0 g (0.02 mole) trichloromethyl chloroformate were added dropwise over 5 hors. After completion of the dropwise addition, stirring was continued for additional 2 hours. After completion of the reaction, the reaction mixture was filtered and the filtrate was concentrated to obtain 4.0 g of 2-trifluoromethyl-4-methyl-thiazole-5-carboxylic acid chlroide. Its purity and yield were 95.0% and 90.0%, respectively. NMR ($\delta^{CDCl_3}$/TMS, ppm): 2.75(3H,s).

EXAMPLE 4

In a similar apparatus to Example 1, 10.4 g (0.06 mole) of 2-methoxy-4-methylthiazole-5-carboxylic acid were suspended in 150 ml of chlorobenzene. Under heating and reflux, phosgene was blown at a rate of 400 ml/hr for 15 hours (0.27 mole). After completion of the blowing, stirring was continued for additional 2 hours. After completion of the reaction, the reaction mixture was filtered and the filtrate was concentrated to obtain 10.9 g of 2-methoxy-4-methylthiazole-5-carboxylic acid chloride. Its purity and yield were 95.0% and 90.0%, respectively. NMR ($\delta^{CDCl_3}$/TMS, ppm): 2.70(3H,s), 3.85(3H,s).

EXAMPLE 5

In a similar apparatus to Example 1,5.7 g (0.04 mole) of 2-methylthiazole-5-carboxylic acid were suspended in 100 ml of toluene. Under heating and reflux, phosgene was blown at a rate of 390 ml/hr for 10 hours (0.17 mole). After completion of the blowing, stirring was continued for additional 2 hours. After completion of the reaction, the reaction mixture was filtered and the filtrate was concentrated to obtain 5.7 g of 2-methylthiazole-5-carboxylic acid chloride. Its purity and yield were 95.0% and 95.0%, respectively. NMR ($\delta^{CDCl_3}$/TMS, ppm): 2.79(3H,s).

EXAMPLE 6

In a similar apparatus to Example 1,7.9 g (0.05 mole) of 4-ethylthiazole-5carboxylic acid were suspended in 100 ml of toluene. Under heating and reflux, phosgene was blown at a rate of 220 ml/hr for 15 hours (0.15 mole). After completion of the blowing, stirring was continued for additional 2 hours. After completion of the reaction, the reaction mixture was filtered and the filtrate was concentrated to obtain 8.5 g of 4-ethyl-thiazole-5carboxylic acid chloride. Its purity and yield were 95.0% and 92.0%, respectively. NMR ($\delta^{CDCl_3}$/TMS, ppm): 1.28(3H,t,J=7Hz), 3.10(2H,q,J=7Hz).

EXAMPLE 7

In a similar apparatus to Example 1, 8.6 g (0.05 mole) of 2-methyl-4-ethylthiazole-5carboxylic acid were suspended in 200 ml of toluene. Under heating and reflux, phosgene was blown at a rate of 340 ml/hr for 12 hours (0.18 mole). After completion of the reaction, the reaction mixture was filtered and the filtrate was concentrated to obtain 9.2 g of 2-methyl-4-ethylthiazole-5-carboxylic acid chloride. Its purity and yield were 96.0% and 96.6%, respectively. NMR ($\delta^{CDCl_3}$/TMS, ppm): 1.25(3H,t,J=8Hz), 2.46(3H,s), 3.06(2H,q,J=8Hz).

EXAMPLE 8

In a similar apparatus to Example 1, 8.6 g (0.05 mole) of 2-ethyl-4methylthiazole-5carboxylic acid were suspended in 200 ml of toluene. Under heating and reflux, phosgene was blown at a rate of 350 ml/hr for 11 hours (0.17 mole). After completion of the reaction, the reaction mixture was filtered and the filtrate was concentrated to obtain 9.3 g of 2-ethyl-4-methylthiazole-5-carboxylic acid chloride. Its purity and yield were 94.5% and 97.5%, respectively. NMR ($\delta^{CDCl_3}$/TMS, ppm):1.36(3H,t,J=8Hz), 2.62(3H,s), 2.93(2H,q,J=8Hz).

EXAMPLE 9

In a similar apparatus to Example, 1, 7.4 g (0.04 mole) of 2-propyl-4-methylthiazole-5-carboxylic acid were suspended in 200 ml of toluene. Under heating and reflux, 11.0 g (0.06 mole) of trimethyl chloroformate were added dropwise for 5 hours. After completion of the reaction, the reaction mixture was filtered and the filtrate was concentrated to obtain 7.9 g of 2-propyl-4-methylthiazole-5-carboxylic acid chloride. Its purity and yield were 95.0% and 97.1%, respectively. NMR ($\delta^{CDCl_3}$/TMS, ppm): 1.00(3H,t,J=7Hz), 1.80(2H,m,J=7Hz), 2.72(3H,s), 2.95(2H,t,J=7Hz).

EXAMPLE 10

In a similar apparatus to Example 1, 15.7 g (0.1 mole) of 2,4-dimethylthiazole-5-carboxylic acid were suspended in 100 ml of toluene, followed by the addition of 0.1 g of N,N-dimethylformamide. Under heating and reflux, phosgene was blown at a rate of 1.3 l/hr for 5 hours (0.29 mole). After completion of the reaction, the reaction mixture was filtered and the filtrate was concentrated to obtain 17.2 g of 2,4-dimethylthiazole-5-carboxylic acid chloride. Its purity and yield were 97.5% and 98.0%, respectively.

EXAMPLE 11

In a similar apparatus to Example 1, 10.7 g (0.06 mole) of 2-chloror-4-methylthiazole-5-carboxylic acid were suspended din 200 ml of butyl acetate, followed by the addition of 0.02 g of N-formyl-piperidine. Under heating and reflux, 15.8 g (0.08 mole) of trimethyl chloroformate were added dropwise over 4 hours. After completion of the dropwise addition, stirring was continued for additional 2 hours. After completion of the reaction, the reaction mixture was filtered and the filtrate was concentrated to obtain 12.1 g of 2-chloro-4-merulthiazole-5-carboxylic acid chloride. Its purity and yield were 98.5% and 96.9%, respectively.

EXAMPLE 12

In a similar apparatus to Example 1, 4.2 g (0.02 mole) of 2-trifluoromethyl-4-methylthiazole-5-carboxylic acid were suspended in 100 ml of chlorobenzene, followed by the addition of 0.04 g of pyridine. Under heating and reflux, 9.9 g (0.05 mole) of trichloromethyl chloroformate were added dropwise over 5 hours. After completion of the dropwise addition, stirring was continued for additional 2 hours. After completion of the reaction, the reaction mixture was filtered and the filtrate was concentrated to obtain 4.5 g of 2-trifluoromethyl-4-methylthiazole-5-carboxylic acid chloride. Its purity and yield were 98.7% and 98.0%, respectively.

EXAMPLE 13

In a similar apparatus to Example 1, 10.4 g (0.06 mole) of 2-methoxy-4-methylthiazole-5carboxylic acid were suspended in 150 ml of tetrahydrofuran, followed by the addition of 0.02 g of N,N-dimethyl-acetamide. Under heating and reflux, phosgene was blown at a rate of 1.1 l/hr for 4.5 hours (0.23 mole). After completion of the blowing, stirring was continued for additional 2 hours. After completion of the reaction, the reaction mixture was filtered and the filtrate was concentrated to obtain 10.8 g of 2-methoxy-4-methylthiazole-5-carboxylic acid chloride. Its purity and yield were 96.2% and 93.9%, respectively.

EXAMPLE 14

In a similar apparatus to Example 1, 10.0 g (0.07 mole) of 2-methylthiazole-5-carboxylic acid were suspended in 100 ml of xylene, followed by the addition of 0.03 g of triethylenediamine. Under heating and reflux, phosgene was blown at a rate of 930 ml/hr for 6 hours (0.25 mole). After completion of the blowing, stirring was continued for additional 2 hours. After completion of the reaction, the reaction mixture was filtered and the filtrate was concentrated to obtain 10.5 g of 2-methylthiazole-5-carboxylic acid chloride. Its purity and yield were 96.0% and 92.8%, respectively.

EXAMPLE 15

In a similar apparatus to Example 1, 7.2 g (0.05 mole) of 4-methylthiazole-5-carboxylic acid were suspended in 100 ml of toluene, followed by the addition of 0.02 g of hexamethylphosphoramide Under heating and reflux, phosgene was blown at a rate of 1.2 l/hr for 2.5 hours (0.13 mole). After completion of the blowing, stirring was continued for additional 2 hours. After completion of the reaction, the reaction mixture was filtered and the filtrate was concentrated to obtain 8.0 g of 4-methylthiazole-5-carboxylic acid chloride. Its purity and yield were 99.2% an d99.0%, respectively. NMR ($\delta^{CDCl_3}$/TMS, ppm): 2.88(3H,s).

EXAMPLE 16

In a similar apparatus to Example 1, 18.8 g (0.11 mole) of 2-methyl-4ethylthiazole-5carboxylic acid were suspended in 150 ml of toluene, followed by the addition of 0.1 g of N,N-dimethylformamide. Under heating and reflux, phosgene was blown at a rate of 1.5 l/hr for 4 hours (0.27 mole). After completion of the reaction, the reaction mixture was filtered and the filtrate was concentrated to obtain 20.3 g of 2-methyl-4-ethyl-thiazole-5-carboxylic acid chloride. Its purity and yield were 98.0% and 97.5%, respectively.

EXAMPLE 17

In a similar apparatus to Example 1, 15.0 g (0.09 mole) of 2-ethyl-4-methylthiazole-5-carboxylic acid were suspended in 150 ml of toluene, followed by the addition of 0.1 g of N,N-dimethylacetamide. Under heating and reflux, phosgene was blown at a rate of 1.5 l/hr for 3.5 hours (0.23 mole). After completion of the reaction, the reaction mixture was filtered and the filtrate was concentrated to obtain 16.1 g of 2-ethyl-4-methylthiazole-5-carboxylic acid chloride. Its purity and yield were 98.2% and 96.9%, respectively.

EXAMPLE 18

In a 200-ml three-neck flask, 15.0 g (0.08 mole) of 2-propyl-4-methylthiazole-5-carboxylic acid were suspended in 100 ml of xylene, followed by the addition of 0.05 g of N,N-dimethylformamide. Under heating and reflux, phosgene was blown at a flow rate of 1.5 l/hr for 3 hours (0.20 mole). After completion of the reaction, the reaction mixture was filtered and the filtrate was concentrated to obtain 16.2 g of 2-propyl-4 -methyl-thiazole-5-carboxylic acid chloride. Its purity and yield were 97.3% and 98.2%, respectively.

COMPARATIVE EXAMPLE 1

15.7 g (0.1 mole) of 2,4-dimethylthiazole-5-carboxylic acid were suspended in 300 ml of ethyl ether and 8 g (0.1 mole) of pyridine, followed by the dropwise addition of 12 g (0.1 mole) of thionyl chloride at −3° C. for 45 minutes. After completion of the reaction, filtration and concentrating were conducted to obtain 7.2 g pf 2.4-dimethylthiazole-5-carboxylic acid chloride. Its purity and yield were 85% and 35%, respectively.

COMPARATIVE EXAMPLE 2

In a similar apparatus to Example 1, 15.7 g (0.1 mole) of 2,4-dimethylthiazole-5carboxylic acid were suspended in 100 ml of toluene. Under heating and reflux, phosgene was blown at a rate of 1.3 l/hr for 5 hours (0.29 mole). After completion of the reaction, the residue was filtered off and the filtrate was concentrated. As a result, 7.2 g of 2,4-dimethyl-thiazole-5-carboxylic acid chloride were obtained. Its purity and yield were 96.9% an 41.0%, respectively.

According to the process of the present invention, each desired compound can be obtained in a shorter reaction time at high purity and yield without need for processing of byproducts while enjoying easy controllabilty of the reaction.

CAPABILITY OF EXPLOITATION IN INDUSTRY

High-purity thiazolecarboxylic acid chlorides available in accordance with the process of the present invention can be used in next steps as intermediates for pharmaceutical products or agricultural chemicals without need for purification. Therefore, the process of the present invention is a process extremely useful in the industry.

We claim:

1. A process for the preparation of a thiazole-carboxylic acid chloride represented by the following general formula (II):

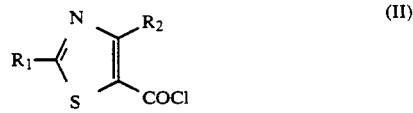

wherein $R_1$ represents a hydrogen or halogen atom, a lower alkyl group, a lower alkoxy group, or a lower alkyl group substituted by a hologen atom or lower alkoxy group, and $R_2$ represents a hydrogen atom, a lower alkyl group, or a lower alkyl group substituted by a halogen atom or lower alkoxy group, which comprises reacting a thiazolecarboxylic acid represented by the following general formula (I):

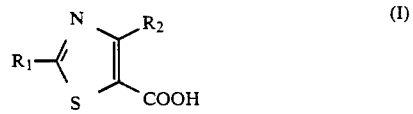

wherein $R_1$ an $R_2$ have the same meanings as defined with respect to formula (II), with phosgene or trichloromethyl chloroformate in the presence or absence of a catalyst.

2. The process of claim 1, wherein the catalyst is selected from N-substituted amides, N-substituted formamides, organic bases and phosphorus amides.

3. The process of claim 1, wherein the thiazolecarboxylic acid represented by the general formula (I) is reacted with phosgene.

4. The process of claim 1, wherein the thiazolecarboxylic acid represented by the general formula (I) is reacted with trichloromethyl chloroformate.

5. The process of claim 2, wherein the catalyst is an N-substituted amide.

6. The process of claim 2, wherein the catalyst is an N-substituted formamide.

7. The process of claim 2, wherein the catalyst is an organic base.

8. The process of claim 2, wherein the catalyst is a phosphoramide.